(12) United States Patent
Andree et al.

(10) Patent No.: US 6,200,935 B1
(45) Date of Patent: Mar. 13, 2001

(54) ARYLALKYLTRIAZOLE DERIVATIVES AND THEIR USE AS HERBICIDES

(75) Inventors: Roland Andree; Mark-Wilhelm Drewes, both of Langenfeld; Andreas Lender, Wuppertal; Karl-Heinz Linker, Leverkusen; Otto Schallner, Monheim, all of (DE); Markus Dollinger, Knox Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/341,765
(22) PCT Filed: Jan. 10, 1998
(86) PCT No.: PCT/EP98/00109
§ 371 Date: Jul. 16, 1999
§ 102(e) Date: Jul. 16, 1999
(87) PCT Pub. No.: WO98/32745
PCT Pub. Date: Jul. 30, 1998

(30) Foreign Application Priority Data

Jan. 24, 1997 (DE) .............................. 197 02 435

(51) Int. Cl.⁷ ...................... A01N 43/653; C07D 249/12
(52) U.S. Cl. ................... 504/273; 548/263.4; 548/263.6
(58) Field of Search ............................ 548/263.4, 263.6; 504/273

(56) References Cited

U.S. PATENT DOCUMENTS

| | | | |
|---|---|---|---|
| 4,249,934 | 2/1981 | Wakabayashi et al. | 71/92 |
| 5,262,390 | 11/1993 | Theodoridis | 504/273 |
| 5,399,543 | 3/1995 | Theodoridis | 504/243 |
| 5,411,980 | 5/1995 | Ashton et al. | 514/384 |

FOREIGN PATENT DOCUMENTS

| | | |
|---|---|---|
| 1200824 | 9/1965 | (DE) . |
| 4416868 | 11/1994 | (DE) . |
| 58-225070 | 12/1983 | (JP) . |
| 96/21647 | 7/1996 | (WO) . |

OTHER PUBLICATIONS

J. Org. Chem. 56, Sep. 13, 1991, pp. 5643–5651.
G. Theodoridis, Pesticide Sci., Aug. 1973, pp. 283–290.

Primary Examiner—Patricia L. Morris
(74) Attorney, Agent, or Firm—Joseph C. Gil

(57) ABSTRACT

The invention relates to novel arylalkyl compounds of the general formula (I)

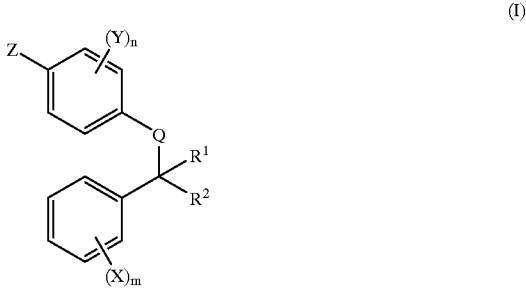

in which
  m represents the numbers 0 to 5,
  n represents the numbers 0 to 4,
  Q represents O, S, SO or $SO_2$,
  $R^1$ represents hydrogen or optionally substituted alkyl,
  $R^2$ represents hydrogen or optionally substituted alkyl,
  X represents hydroxyl, mercapto, amino, hydroxyamino, nitro, formyl, carboxyl, cyano, carbamoyl, thiocarbamoyl, halogen, or represents an in each case optionally cyano-, halogen- or alkoxy-substituted radical from the series alkyl, alkoxy, alkylthio, alkylsulphinyl, alkylsulphonyl, alkylamino, dialkylamino, alkylcarbonyl or alkoxycarbonyl,
  Y represents nitro, carboxyl, cyano, carbamoyl, thiocarbamoyl, halogen, or represents an in each case optionally cyano-, halogen- or alkoxy-substituted radical from the series alkyl, alkoxy, alkylthio, alkylsulphinyl or alkylsulphonyl, and
  Z represents one of the groupings below

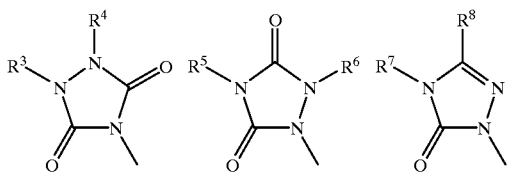

in which
  $R^3$, $R^4$, $R^5$, $R^6$ and $R^7$ are each as defined in the description,
to processes for their preparation, to novel intermediates and to the use of the arylalkyl compounds as herbicides.

7 Claims, No Drawings

ARYLALKYLTRIAZOLE DERIVATIVES AND THEIR USE AS HERBICIDES

TECHNICAL FIELD OF THE INVENTION

The invention relates to novel arylalkyl compounds, to processes for their preparation, to novel intermediates and to their use as herbicides.

BACKGROUND OF THE INVENTION

Some arylalkyl compounds have already been disclosed in the (patent) literature as potential herbicides (cf. DE 2526358, U.S. Pat. No. 4,249,934, U.S. Pat. No. 5,262,390, WO 9621647). However, these compounds have not attained any practical importance worth mentioning.

DETAILED DESCRIPTION OF THE INVENTION

This invention, accordingly, provides novel arylalkyl compounds of the general formula (I)

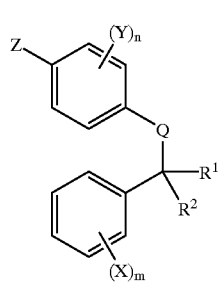

(I)

in which
m represents the numbers 0 to 5,
n represents the numbers 0 to 4,
Q represents O, S, SO or $SO_2$,
$R^1$ represents hydrogen or optionally substituted alkyl,
$R^2$ represents hydrogen or optionally substituted alkyl,
X represents hydroxyl, mercapto, amino, hydroxyamino, nitro, formyl, carboxyl, cyano, carbamoyl, thiocarbamoyl, halogen, or represents an in each case optionally cyano-, halogen- or alkoxy-substituted radical from the series alkyl, alkoxy, alkylthio, alkylsulphinyl, alkylsulphonyl, alkylamino, dialkylamino, alkylcarbonyl or alkoxycarbonyl,
Y represents nitro, carboxyl, cyano, carbamoyl, thiocarbamoyl, halogen, or represents an in each case optionally cyano-, halogen- or alkoxy-substituted radical from the series alkyl, alkoxy, alkylthio, alkylsulphinyl or alkylsulphonyl, and
Z represents one of the groupings below

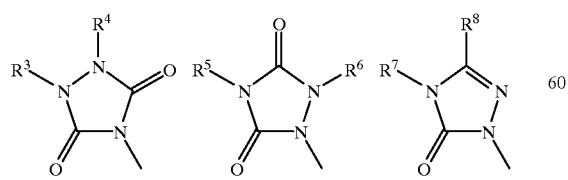

in which
$R^3$ represents hydrogen, cyano, formyl, or represents an in each case optionally cyano-, halogen- or alkoxy-substituted radical from the series alkyl, alkylcarbonyl, alkoxycarbonyl, alkenyl or alkinyl,
$R^4$ represents hydrogen, cyano, formyl, or represents an in each case optionally cyano-, halogen- or alkoxy-substituted radical from the series alkyl, alkylcarbonyl, alkoxycarbonyl, alkenyl or alkinyl,
$R^5$ represents hydrogen, cyano, formyl, or represents an in each case optionally cyano-, halogen- or alkoxy-substituted radical from the series alkyl, alkylcarbonyl, alkoxycarbonyl, alkenyl or alkinyl,
$R^6$ represents hydrogen, cyano, formyl, or represents an in each case optionally cyano-, halogen- or alkoxy-substituted radical from the series alkyl, alkylcarbonyl, alkoxycarbonyl, alkenyl or alkinyl,
$R^7$ represents hydrogen, amino, cyano, formyl, or represents an in each case optionally cyano-, halogen- or alkoxy-substituted radical from the series alkyl, alkoxy, alkylamino, dialkylamino, alkylcarbonyl, alkoxycarbonyl, alkenyl, alkinyl or cycloalkyl, and
$R^8$ represents hydrogen, halogen, or represents an in each case optionally cyano-, halogen- or alkoxy-substituted radical from the series alkyl, alkoxy, alkylthio, alkylsulphinyl, alkylsulphonyl, alkyl amino, dialkylamino, alkenyl, alkenyloxy, alkenylthio, alkenylamino, alkinyl, alkinyloxy, alkinylthio, cycloalkyl, cycloalkyloxy, cycloalkylthio or cycloalkylamino, or together with $R^7$ represents alkanediyl (alkylene).

The novel arylalkyl compounds of the general formula (I) are obtained when
(a) 4-aryl-semicarbazides of the general formula (II)

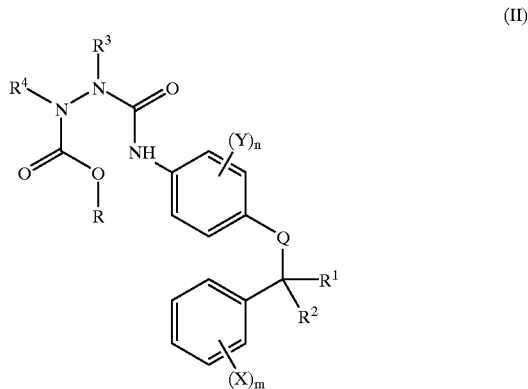

(II)

in which
m, n, Q, $R^1$, $R^2$, $R^3$, $R^4$, X and Y are each as defined above and
R represents alkyl
are cyclocondensed, if appropriate in the presence of a reaction auxiliary and if appropriate in the presence of a diluent, and, if appropriate, subsequently electrophilic or nucleophilic substitution reactions within the scope of the definition of the substituents are carried out in a customary manner on the product, or when (b) 1-aryl-semicarbazides of the general formula (III)

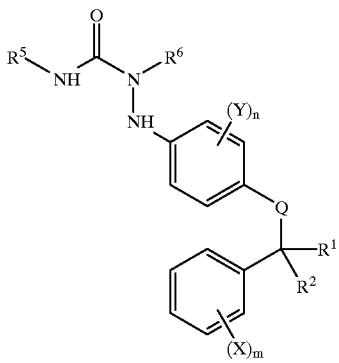

(III)

in which m, n, Q, $R^1$, $R^2$, $R^5$, $R^6$, X and Y are each as defined above are reacted with phosgene, if appropriate in the presence of a reaction auxiliary and if appropriate in the presence of a diluent, and, if appropriate, subsequently electrophilic or nucleophilic substitution reactions within the scope of the definition of the substituents are carried out in a customary manner on the product, or when (c) halogenoarenes of the general formula (IV)

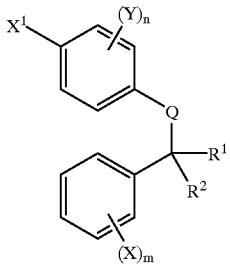

(IV)

in which m, n, Q, $R^1$, $R^2$, X and Y are each as defined above and $X^1$ represents halogen are reacted with heterocyclic compounds of the general formula (V)

Z—H (V)

in which

Z is as defined above, if appropriate in the presence of a reaction auxiliary and if appropriate in the presence of a diluent, and, if appropriate, subsequently electrophilic or nucleophilic substitution reactions within the scope of the definition of the substituents are carried out in a customary manner on the product, or when (d) arylalkyl halides of the general formula (VI)

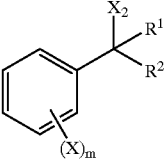

(VI)

in which m, $R^1$, $R^2$ and X are each as defined above and $X^2$ represents halogen are reacted with are each of the general formula (VII)

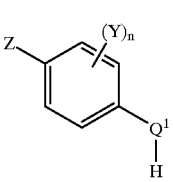

(VII)

in which n, Y and Z are each as defined above and $Q^1$ represents oxygen or sulphur, if appropriate in the presence of a reaction auxiliary and if appropriate in the presence of a diluent, and, if appropriate, subsequently electrophilic or nucleophilic substitution reactions within the scope of the definition of the substituents are carried out in a customary manner on the product.

The compounds of the general formula (I) can also be converted by other customary methods into other compounds of the general formula (I) according to the above definition, for example by customary conversions of carboxylic acid groupings or their derivatives (for example X: COOH→COOCH$_3$, COOCH$_3$→CONH$_2$, CONH$_2$→CN, CN→CSNH$_2$), by alkylation reactions (for example $R^3$, $R^4$, $R^5$, $R^6$: H→CH$_3$ or CHF$_2$) or by oxidation (for example Q: S→SO or SO$_2$)—cf. also the Preparation Examples.

The novel substituted arylalkyl compounds of the general formula (I) have strong herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably represents fluorine, chlorine or bromine, in particular represents fluorine or chlorine.

The invention preferably provides compounds of the formula (I) in which m represents the numbers 0 to 4, n represents the numbers 0 to 3, Q represents O, S, SO or SO$_2$, $R^1$ represents hydrogen or represents optionally halogen-substituted alkyl having 1 to 6 carbon atoms, $R^2$ represents hydrogen or represents optionally halogen-substituted alkyl having 1 to 6 carbon atoms, X represents hydroxyl, mercapto, amino, hydroxyamino, nitro, formyl, carboxyl, cyano, carbamoyl, thiocarbamoyl, halogen, or represents an in each case optionally cyano-, halogen- or $C_1$–$C_4$-alkoxy-substituted radical from the series alkyl, alkoxy, alkylthio, alkylsulphinyl, alkylsulphonyl, alkylamino, dialkylamino, alkylcarbonyl or alkoxycarbonyl having in each case 1 to 6 carbon atoms in the alkyl groups, Y represents nitro, carboxyl, cyano, carbamoyl, thiocarbamoyl, halogen, or represents an in each case optionally cyano-, halogen- or $C_1$–$C_4$-alkoxy-substituted radical from the series alkyl, alkoxy, alkylthio, alkylsulphinyl or alkylsulphonyl having in each case 1 to 6 carbon atoms in the alkyl groups, and Z represents one of the groupings below

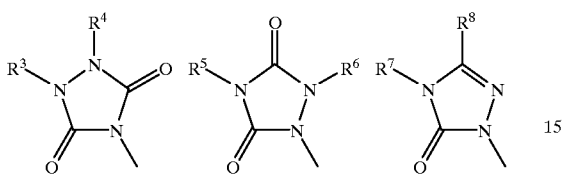

in which $R^3$ represents hydrogen, cyano, formyl, or represents an in each case optionally cyano-, halogen- or $C_1$–$C_4$-alkoxy-substituted radical from the series alkyl, alkylcarbonyl or alkoxycarbonyl having in each case 1 to 6 carbon atoms in the alkyl groups, or represents in each case optionally halogen-substituted alkenyl or alkinyl having in each case 2 to 6 carbon atoms, $R^4$ represents hydrogen, cyano, formyl, or represents an in each case optionally cyano-, halogen- or $C_1$–$C_4$-alkoxy-substituted radical from the series alkyl, alkylcarbonyl or alkoxycarbonyl having in each case 1 to 6 carbon atoms in the alkyl groups, or represents in each case optionally halogen-substituted alkenyl or alkinyl having in each case 2 to 6 carbon atoms, $R^5$ represents hydrogen, cyano, formyl, or represents an in each case optionally cyano-, halogen- or $C_1$–$C_4$-alkoxy-substituted radical from the series alkyl, alkylcarbonyl or alkoxycarbonyl having in each case 1 to 6 carbon atoms in the alkyl groups, or represents in each case optionally halogen-substituted alkenyl or alkinyl having in each case 2 to 6 carbon atoms, $R^6$ represents hydrogen, cyano, formyl, or represents an in each case optionally cyano-, halogen- or $C_1$–$C_4$-alkoxy-substituted radical from the series alkyl, alkylcarbonyl or alkoxycarbonyl having in each case 1 to 6 carbon atoms in the alkyl groups, or represents in each case optionally halogen-substituted alkenyl or alkinyl having in each case 2 to 6 carbon atoms, $R^7$ represents hydrogen, amino, cyano, formyl, or represents an in each case optionally cyano-, halogen- or $C_1$–$C_4$-alkoxy-substituted radical from the series alkyl, alkoxy, alkylamino, dialkylamino, alkylcarbonyl or alkoxycarbonyl having in each case 1 to 6 carbon atoms in the alkyl groups, or represents in each case optionally halogen-substituted alkenyl or alkinyl having in each case 2 to 6 carbon atoms, or represents optionally cyano- or halogen-substituted cycloalkyl having 3 to 6 carbon atoms, and $R^8$ represents hydrogen, halogen, or represents an in each case optionally cyano-, halogen- or $C_1$–$C_4$-alkoxy-substituted radical from the series alkyl, alkoxy, alkylthio, alkylsulphinyl, alkylsulphonyl, alkylamino or dialkylamino having in each case 1 to 6 carbon atoms in the alkyl groups, or represents an in each case optionally halogen-substituted radical from the series alkenyl, alkenyloxy, alkenylthio, alkenylamino, alkinyl, alkinyloxy or alkinylthio having in each case 2 to 6 carbon atoms, or represents an in each case optionally cyano- or halogen-substituted radical from the series cycloalkyl, cycloalkyloxy, cycloalkylthio or cycloalkylamino having in each case 3 to 6 carbon atoms, or together with $R^7$ represents alkanediyl (alkylene) having 2 to 6 carbon atoms.

The invention in particular relates to compounds of the formula (I) in which m represents the numbers 0, 1, 2 or 3, n represents the numbers 0, 1 or 2, Q represents O, S, SO or $SO_2$, $R^1$ represents hydrogen or represents in each case optionally fluorine- and/or chlorine-substituted methyl, ethyl, n- or i-propyl, n-, i-, s- or t-butyl, $R^2$ represents hydrogen or represents in each case optionally fluorine- and/or chlorine-substituted methyl, ethyl, n- or i-propyl, n- or i-butyl, X represents hydroxyl, mercapto, amino, hydroxyamino, nitro, formyl, carboxyl, cyano, carbamoyl, thiocarbamoyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, propylsulphinyl, methylsulphonyl, ethylsulphonyl, propylsulphonyl, methylamino, ethylamino, n- or i-propylamino, n-, i-, s- or t-butylamino, dimethylamino, diethylamino, acetyl, propionyl, methoxycarbonyl or ethoxycarbonyl, Y represents nitro, carboxyl, cyano, carbamoyl, thiocarbamoyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl or ethylsulphonyl, and Z represents one of the groupings below

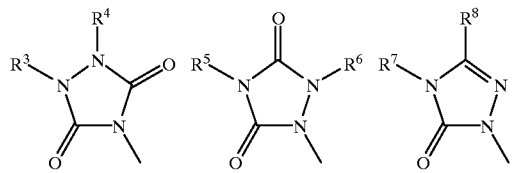

in which $R^3$ represents hydrogen, cyano, formyl, or represents in each case optionally cyano-, fluorine-, chlorine-, methoxy- or ethoxy-substituted methyl, ethyl, n- or i-propyl, n-, i-, s- or t-butyl, acetyl, propionyl, methoxycarbonyl or ethoxycarbonyl, or represents in each case optionally fluorine-, chlorine- or bromine-substituted propenyl, butenyl, propinyl or butinyl, $R^4$ represents hydrogen, cyano, formyl, or represents in each case optionally cyano-, fluorine-, chlorine-, methoxy- or ethoxy-substituted methyl, ethyl, n- or i-propyl, n-, i-, s- or t-butyl, acetyl, propionyl, methoxycarbonyl or ethoxycarbonyl, or represents in each case optionally fluorine-, chlorine- or bromine-substituted propenyl, butenyl, propinyl or butinyl, R[5] represents hydrogen, cyano, formyl, or represents in each case optionally cyano-, fluorine-, chlorine-, methoxy- or ethoxy-substituted methyl, ethyl, n- or i-propyl, n-, i-, s- or t-butyl, acetyl, propionyl, methoxycarbonyl or ethoxycarbonyl, or represents in each case optionally fluorine-, chlorine- or bromine-substituted propenyl, butenyl, propinyl or butinyl, R[6] represents hydrogen, cyano, formyl, or represents in each case optionally cyano-, fluorine-, chlorine-, methoxy- or ethoxy-substituted methyl, ethyl, n- or i-propyl, n-, i-, s- or t-butyl, acetyl, propionyl, methoxycarbonyl or ethoxycarbonyl, or represents in each case optionally fluorine-, chlorine- or bromine-substituted propenyl, butenyl, propinyl or butinyl, R[7] represents hydrogen, amino, cyano, formyl, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, acetyl, propionyl, methoxycarbonyl or ethoxycarbonyl, or represents in each case optionally fluorine-, chlorine- or bromine-substituted propenyl, butenyl, propinyl or butinyl, or represents optionally cyano-, fluorine-, chlorine- or bromine-substituted cyclopropyl, cyclobutyl, cyclopentyl or cyclohexyl, and R[8] represents hydrogen, fluorine, chlorine, bromine, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, dimethylamino or diethylamino, or represents in each case optionally fluorine-, chlorine- or bromine-substituted propenyl, butenyl, propenyloxy, butenyloxy, propenylthio, butenylthio, propenylamino, butenylamino, propinyl, butinyl, propinyloxy, butinyloxy, propinylthio or butinylthio, or represents in each case optionally cyano-, fluorine-, chlorine- or bromine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

Very particular preference is given to arylalkyl compounds of the general formula (I) in which Z represents one of the groupings below

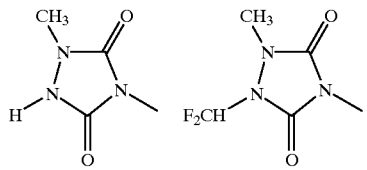

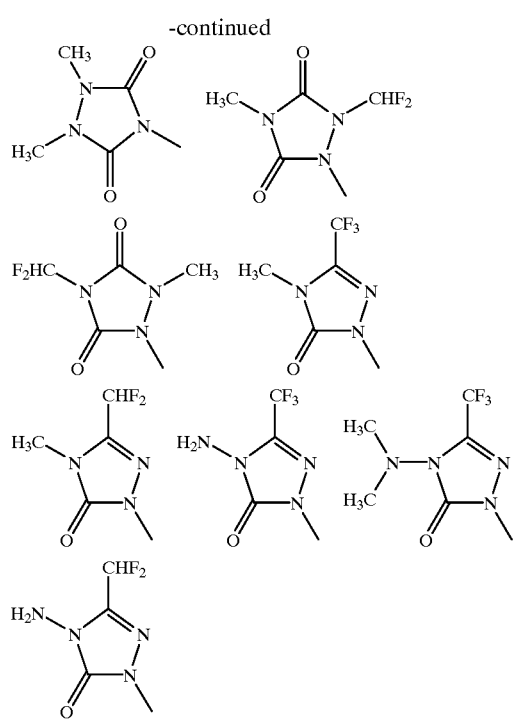

The abovementioned general or preferred radical definitions apply both to the end products of the formula (I) and, correspondingly, to the starting materials or intermediates required in each case for the preparation. These radical definitions can be combined with each other at will, i.e. including combinations between the abovementioned preferred ranges.

Using, for example, 4-[4-(2,4-difluorophenylmethylthio)-phenyl]-1-ethoxycarbonyl-semicarbazide as starting material, the course of the reaction in the process (a) according to the invention can be illustrated by the following scheme:

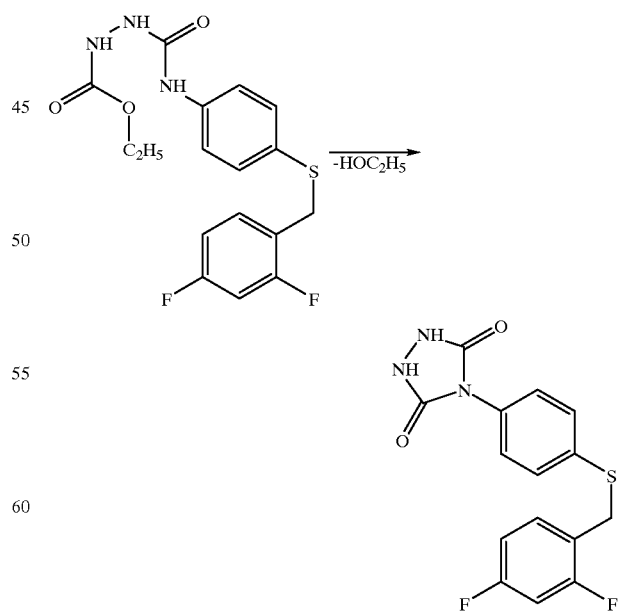

Using, for example, 1-[4-(2,5-dichlorophenylmethylsulphonyl)-phenyl]-4-methyl-semicarbazide and phosgene as starting materials, the course of the reaction in the process (b) according to the invention can be illustrated by the following scheme:

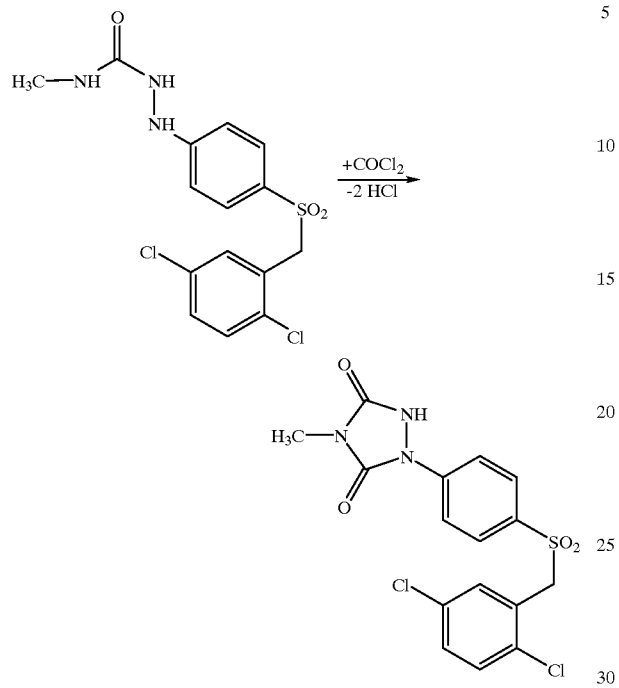

Using, for example, 1-(3-chloro-4-fluoro-phenyl-sulphinyl)-1-(4-bromo-3-methyl-phenyl)-ethane and 4-methyl-5-trifluoromethyl-2,4-dihydro-3H-1,2,4-triazol-3-one as starting materials, the course of the reaction in the process (c) according to the invention can be illustrated by the following scheme:

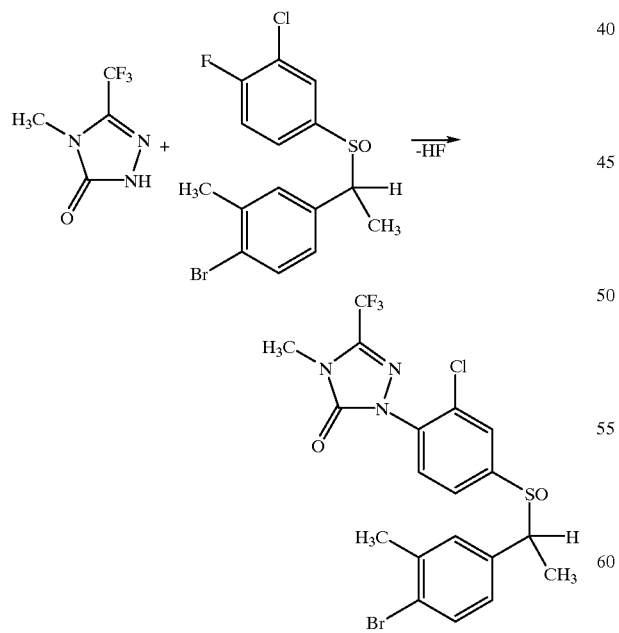

Using, for example, 3-cyano-phenylmethyl chloride and 4-difluoromethyl-5-methyl-2-(2-fluoro-4-hydroxy-phenyl)-2,4-dihydro-3H-1,2,4-triazol-3-one as starting materials, the course of the reaction in the process (d) according to the invention can be illustrated by the following scheme:

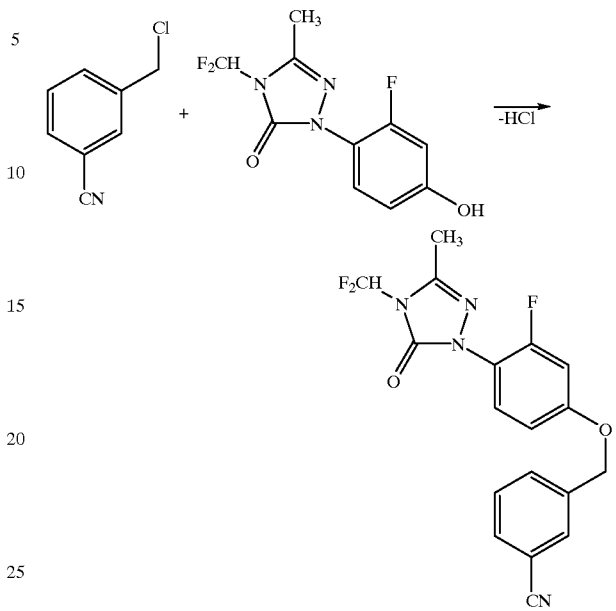

The formula (II) provides a general definition of the 4-aryl-semicarbazides to be used as starting materials in the process (a) according to the invention for preparing compounds of the formula (I). In the formula (II), m, n, Q, $R^1$, $R^2$, $R^3$, $R^4$, X and Y each preferably or in particular have those meanings which have already been mentioned above, in connection with the description of the compounds of the formula (I) according to the invention, as being preferred or as being particularly preferred for m, n, Q, $R^1$, $R^2$, $R^3$, $R^4$, X and Y; R preferably represents alkyl having 1 to 4 carbon atoms, in particular methyl or ethyl.

The starting materials of the formula (II) are hitherto not known from the literature; as novel substances, they also form part of the subject-matter of the present application.

The novel 4-aryl-semicarbazides of the general formula (II) are obtained when amino are each of the general formula (VIII)

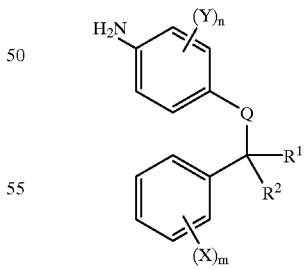

(VIII)

in which m, n, Q, $R^1$, $R^2$, X and Y are each as defined above are reacted with phosgene or diphosgene (trichloroethyl chloroformate) if appropriate in the presence of a diluent, such as, for example, ethyl acetate, at temperatures between 0° C. and 50° C. and then reacted with a hydrazinecarboxylic ester of the general formula (IX)

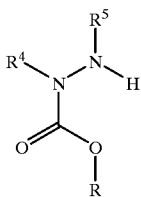

(IX)

in which

R, $R^4$ and $R^5$ are each as defined above, if appropriate in the presence of a diluent, such as, for example, and toluene, at temperatures between 10° C. and 120° C. (cf. the Preparation Examples).

The aminoarenes of the general formula (VIII) required as precursors are known and/or can be prepared by known processes (cf. U.S. Pat. No. 5,399,543).

The hydrazinecarboxylic esters of the general formula (IX) furthermore required as precursors are known chemicals for synthesis.

The formula (III) provides a general definition of the 1-aryl-semicarbazides to be used as starting materials in the process (b) according to the invention for preparing compounds of the formula (I). In the formula (III), m, n, Q, $R^1$, $R^2$, $R^5$, $R^6$, X and Y each preferably or in particular have those meanings which have already been mentioned above, in connection with the description of the compounds of the formula (I) according to the invention, as being preferred or as being particularly preferred for m, n, Q, $R^1$, $R^2$, $R^5$, $R^6$, X and Y; R preferably represents alkyl having 1 to 4 carbon atoms, in particular methyl or ethyl.

The starting materials of the formula (I) have hitherto not been known from the literature; as novel substances, they also form part of the subject-matter of the present application.

The novel 1-aryl-semicarbazides of the general formula (III) are obtained when hydrazinoarenes of the general formula (X)

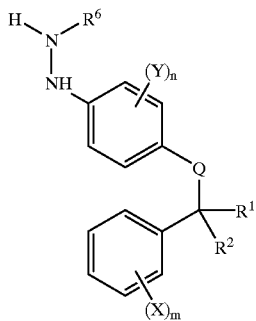

(X)

in which m, n, Q, $R^1$, $R^2$, $R^6$, X and Y are each as defined above are reacted with isocyanates of the general formula (XI)

$$R^5\text{—}N\text{=}C\text{=}O \qquad (XI)$$

in which $R^5$ is as defined above, if appropriate in the presence of a diluent, such as, for example, toluene or chlorobenzene, and if appropriate in the presence of a basic reaction auxiliary, such as, for example, sodium hydride or potassium hydride, potassium t-butoxide, triethyl amine or ethyldiisopropylamine, at temperatures between 10° C. and 150° C.

The hydrazinoarenes of the general formula (X) required as precursors are known and/or can be prepared by known processes (cf. U.S. 5,262,390).

The isocyanates of the general formula (XI) furthermore required as precursors are known chemicals for synthesis.

The formula (IV) provides a general definition of the halogenoarenes to be used as starting materials in the process (c) according to the invention for preparing compounds of the formula (I). In the formula (IV), m, n, Q, $R^1$, $R^2$, X and Y each preferably or in particular have those meanings which have already been mentioned above, in connection with the description of the compounds of the formula (I) according to the invention, as being preferred or as being particularly preferred for m, n, Q, $R^1$, $R^2$, X and Y; $X^1$ preferably represents fluorine, chlorine or bromine, in particular fluorine or chlorine.

The starting materials of the formula (IV) are known and/or can be prepared by known processes (cf. DE 2526358, U.S. Pat. No. 4,249,934, U.S. Pat. No. 5,262,390, WO 9621647).

The formula (V) provides a general definition of the heterocyclic compounds further to be used as starting materials in the process (c) according to the invention. In the formula (V), Z preferably or in particular has that meaning which has already been mentioned above, in connection with the description of the compounds of the formula (I) according to the invention, as being preferred or as being particularly preferred for Z.

The starting materials of the general formula (V) are known and/or can be prepared by known processes (cf. J. Org. Chem. 56 (1991), 5643–5651; DE4416868).

The formula (VI) provides a general definition of the arylalkyl halides to be used as starting materials in the process (d) according to the invention for preparing compounds of the formula (I). In the formula (VI), m, $R^1$, $R^2$ and X each preferably or in particular have those meanings which have already been mentioned above, in connection with the description of the compounds of the formula (I) according to the invention, as being preferred or as being particularly preferred for m, $R^1$, $R^2$ and X; $X^2$ preferably represents chlorine, bromine or iodine, in particular chlorine or bromine.

The starting materials of the general formula (VI) are known chemicals for synthesis.

The formula (VII) provides a general definition of the arenes furthermore to be used as starting materials in the process (d) according to the invention. In the formula (VII), N, Y and Z each preferably or in particular have those meanings which have already been mentioned above, in connection with the description of the compounds of the formula (I) according to the invention, as being preferred or as being particularly preferred for n, Y and Z; $Q^1$ preferably represents O or S, in particular O.

The starting materials of the general formula (VII) are known and/or can be prepared by processes known per se (cf. U.S. Pat. No. 5,262,390).

Suitable reaction auxiliaries for processes (a) to (d) according to the invention are in general the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]octane (DABCO), 1,5-diazabicyclo[4,3,0]-non-5-ene (DBN), or 1,8 diazabicyclo[5,4,0]undec-7-ene (DBU).

Suitable diluents for carrying out the processes (a) to (d) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a) to (d) according to the invention, the reaction temperatures can be varied within a relatively wide range. In general, the reaction is carried out at temperatures between −20° C. and 150° C., preferably between 10° C. and 120° C.

In general, the processes (a) to (d) according to the invention are carried out under atmospheric pressure. However, it is also possible to carry out the processes according to the invention under elevated or reduced pressure—in general between 0.1 bar and 10 bar.

For carrying out the process according to the invention, the starting materials are generally employed in approximately equimolar amounts. However, it is also possible to use one of the components in a relatively large excess. The reaction is generally carried out in a suitable solvent in the presence of a reaction auxiliary, and the reaction mixture is generally stirred for a number of hours at the required temperature. Work-up is carried out by customary methods (cf. the Preparation Examples).

The active compounds according to the invention can be used as defoliants, desiccants, haulm killers and, especially, as weedkillers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and open spaces with or without tree plantings. Equally, the compounds can be employed for the control of weeds in perennial crops for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture land, and for the selective control of weeds in annual crops.

The compounds of the formula (I) according to the invention are particularly suitable for the selective control of monocotyledonous and dicotyledonous weeds in monocotyledonous crops, such as, for example, maize and wheat, both pre-emergence and postemergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifying agents and/or dispersing agents and/or foam-forming agents.

If the extender used is water, it is also possible to employ for example organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulphuron, asulam, atrazine, azimsulphuron, benazolin, benfuresate, bensulphuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulphuron, chlortoluron, cinmethylin, cinosulphuron, clethodim, clodinafop(-propargyl), clomazone, clopyralid, clopyrasulphuron, cloransulam(-methyl), cumyluron, cyanazine, cycloate, cyclosulphamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulphuron(-methyl), ethofumesate, ethoxyfen, etobenzanid, fenoxaprop(-ethyl), flamprop(-isopropyl), flamprop(-isopropyl-L), flamprop(-methyl), flazasulphuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimridol, flurtamone, fomesafen, glufosinate(-ammonium), glyphosate(-isopropyl-ammonium), halosafen, haloxyfop(-ethoxyethyl), hexazinone, imazamethabenz(-methyl), imazamethapyr, imazamox, imazapyr, imazaquin, imazethapyr, imazosulphuron, ioxynil, isopropalin, isoproturon, isoxaben, isoxaflutole, isoxapyrifop, lactofen, lenacil, linuron, MCPA, MCPP, mefenacet, metamitron,
metazachlor, methabenzthiazuron, metobenzuron, metobromuron, metolachlor, metosulam, metoxuron, metribuzin, metsulphuron(-methyl), molinate, monolinuron, naproanilide, napropamide, neburon, nicosulphuron, norflurazon orbencarb, oryzalin, oxadiazon, oxyfluorfen, paraquat, pendimethalin, phenmedipham, piperophos, pretilachlor, primisulphuron(-methyl), prometryn, propachlor, propanil, propaquizafop, propyzamide, prosulphocarb, prosulphuron, pyrazolate, pyrazosulphuron(-ethyl), pyrazoxyfen, pyributicarb, pyridate, pyrithiobac(-sodium), quinchlorac, quinmerac, quizalofop(-ethyl), quizalofop(-p-tefuryl), rimsulphuron, sethoxydim, simazine, simetryn, sulcotrione, sulphentrazone, sulphometuron(-methyl), sulphosate, tebutam, tebuthiuron, terbuthylazine, terbutryn, thenylchlor, thiafluamide, thiazopyr, thidiazimin, thifensulphuron(-methyl), thiobencarb, tiocarbazil, tralkoxydim, triallate, triasulphuron, tribenuron(-methyl), triclopyr, tridiphane, trifluralin and triflusulphuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

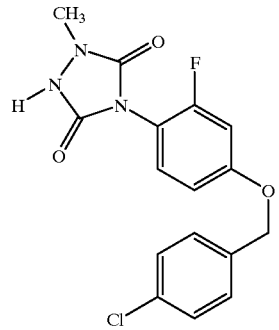

(Process (a))

At room temperature (20° C.), 5.0 g (13 mMol) of 1-ethoxycarbonyl-2-methyl-4-[4-(4-chloro-phenyl-methoxy)-2-fluoro-phenyl]-semicarbazide are added with stirring to a solution of 7.2 g (0.13 mol) of potassium hydroxide in 32 ml of water, and the reaction mixture is stirred at 80° C. for one hour. After cooling to room temperature, the pH value of the mixture is adjusted to 5 by addition of 2N hydrochloric acid and the crystalline product is isolated by filtration with suction.

This gives 4.0 g (89% of theory) of 4-[(4-chloro-phenyl-methoxy)-2-fluoro-phenyl]-1-methyl-1,2,4-triazolin-2,5-dione of melting point 172° C.

Example 2

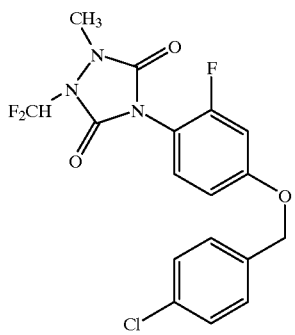

(Subsequent Reaction)

A mixture of 2.0 g (5.7 mMol) of 4-[(4-chloro-phenyl-methoxy)-2-fluoro-phenyl]-1-methyl-1,2,4-triazolin-2,5-dione, 1.57 g (11.4 mMol) of potassium carbonate and 30 ml of N,N-dimethylformamide is stirred at 60° C. for one hour. The mixture is then heated to 80° C., and chlorodifluoromethane is introduced at this temperature for 2 hours. After cooling to room temperature (about 20° C.), the mixture is poured into approximately the same amount by volume of 1N hydrochloric acid and shaken with ethyl acetate. The organic phase is separated off, dried with sodium sulphate and filtered. The filtrate is concentrated under water pump vacuum and the residue is purified by column chromatography (silica gel/methylene chloride).

This gives 1.6 g (70% of theory) of 4-[(4-chloro-phenyl-methoxy)-2-fluoro-phenyl]-2-difluoromethyl-1-methyl-1,2,4-triazolin-2,5-dione of melting point 85° C.

Example 3

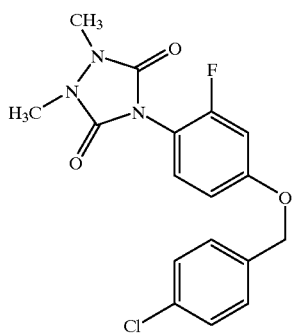

(Subsequent Reaction)

A mixture of 1.5 g (4.3 mMol) of 4-[(4-chloro-phenyl-methoxy)-2-fluoro-phenyl]-1-methyl-1,2,4-triazolin-2,5-dione, 0.6 g (4.7 mMol) of dimethyl sulphate, 0.65 g (4.7 mMol) of potassium carbonate and 50 ml of acetonitrile is stirred at room temperature (about 20° C.) for 18 hours and then concentrated under water pump vacuum. The residue is digested with ethyl acetate and filtered. The solvent is carefully distilled off from the filtrate under water pump vacuum.

This gives 1.1 g (71% of theory) of 4-[(4-chloro-phenyl-methoxy)-2-fluoro-phenyl]-1,2-dimethyl-1,2,4-triazolin-2,5-dione as a crystalline residue of melting point 132° C.

Similarly to the Preparation Examples 1 to 3, and in accordance with the general description of the preparation processes according to the invention, it is also possible to prepare, for example, the compounds of the formula (I) listed in Table 1 below.

(I)

TABLE 1

Examples of the compounds of the formula (I)

| Ex. No. | m | n | Q | $R^1$ | $R^2$ | (position) X | (position) Y | Z | Physical data |
|---|---|---|---|---|---|---|---|---|---|
| 4 | 1 | 1 | O | H | H | (2-)Cl | (2-)F | 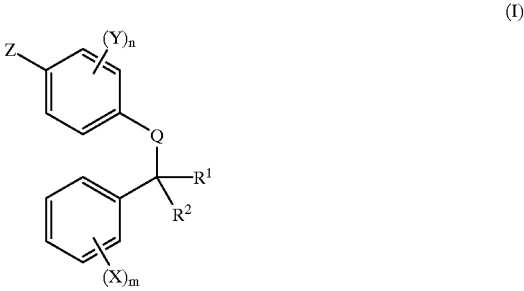 | M.p.: 125° C. |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 5 | 1 | 1 | O | H | H | (3-)Cl | (2-)F | *triazolidinedione* | M.p.: 114° C. |
| 6 | 1 | 1 | O | H | H | (4-)CN | (2-)F | *triazolidinedione* | |
| 7 | 1 | 1 | O | H | H | (4-)CSNH₂ | (2-)F | *triazolidinedione* | |
| 8 | 1 | 0 | O | H | H | (4-)Cl | — | *triazolidinedione* | |
| 9 | 1 | 1 | O | CH₃ | CH₃ | (4-)F | (2-)F | *triazolidinedione* | |
| 10 | 2 | 1 | O | H | H | (2-)F, (5-)CN | (2-)F | *triazolidinedione* | |
| 11 | 3 | 1 | O | H | H | (2-,4-)F₂, (5-)CN | (2-)F | *triazolidinedione* | |
| 12 | 1 | 1 | S | H | H | (4-)Cl | (2-)F | *triazolidinedione* | |

TABLE 1-continued
Examples of the compounds of the formula (I)
| Ex. No. | m | n | Q | R¹ | R² | (position) X | (position) Y | Z | Physical data |
|---|---|---|---|---|---|---|---|---|---|
| 13 | 1 | 1 | O | H | H | (2-)Cl | (2-)F | 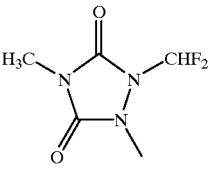 | |
| 14 | 1 | 1 | O | H | H | (3-)Cl | (2-)F | 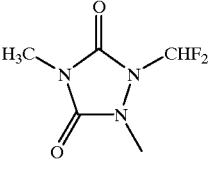 | |
| 15 | 1 | 1 | O | H | H | (4-)CN | (2-)F | 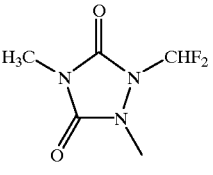 | |
| 16 | 1 | 1 | O | H | H | (4-)CSNH$_2$ | (2-)F | 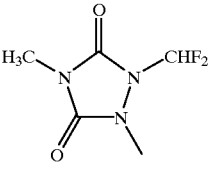 | |
| 17 | 1 | 0 | O | H | H | (4-)Cl | — | 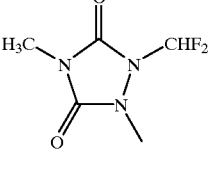 | |
| 18 | 1 | 1 | O | CH$_3$ | CH$_3$ | (4-)F | (2-)F | 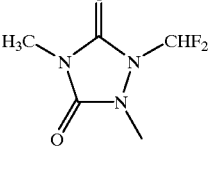 | |
| 19 | 2 | 1 | O | H | H | (2-)F, (5-)CN | (2-)F | 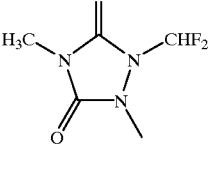 | |
| 20 | 3 | 1 | O | H | H | (2-,4-)F$_2$, (5-)CN | (2-)F | 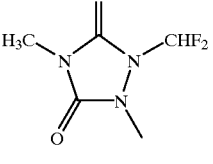 | |

TABLE 1-continued

Examples of the compounds of the formula (I)

| Ex. No. | m | n | Q | R¹ | R² | X (position) | Y (position) | Z | Physical data |
|---|---|---|---|---|---|---|---|---|---|
| 21 | 1 | 1 | O | H | H | (4-)Cl | (2-)F | (triazolidinedione: N-CH₃, N-CHF₂) | |
| 22 | 1 | 1 | O | H | H | (2-)Cl | (2-)F | (triazolidinedione: N-CHF₂, N-CH₃) | |
| 23 | 1 | 1 | O | H | H | (3-)Cl | (2-)F | (triazolidinedione: N-CHF₂, N-CH₃) | |
| 24 | 1 | 1 | O | H | H | (4-)CN | (2-)F | (triazolidinedione: N-CHF₂, N-CH₃) | |
| 25 | 1 | 1 | O | H | H | (4-)CSNH₂ | (2-)F | (triazolidinedione: N-CHF₂, N-CH₃) | |
| 26 | 1 | 0 | O | H | H | (4-)Cl | — | (triazolidinedione: N-CHF₂, N-CH₃) | |
| 27 | 1 | 1 | O | CH₃ | CH₃ | (4-)F | (2-)F | (triazolidinedione: N-CHF₂, N-CH₃) | |
| 28 | 2 | 1 | O | H | H | (2-)F, (5-)CN | (2-)F | (triazolidinedione: N-CHF₂, N-CH₃) | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 29 | 3 | 1 | O | H | H | (2-,4-)F$_2$, (5-)CN | (2-)F | F$_2$HC-triazolidinedione-N(CH$_3$)-N(CH$_3$) | |
| 30 | 1 | 1 | O | H | H | (4-)Cl | (2-)F | F$_2$HC-triazolidinedione-N(CH$_3$)-N(CH$_3$) | |
| 31 | 1 | 1 | O | H | H | (2-)Cl | (2-)F | H$_3$C-N, CF$_3$-triazolinone-N-CH$_3$ | |
| 32 | 1 | 1 | O | H | H | (3-)Cl | (2-)F | H$_3$C-N, CF$_3$-triazolinone-N-CH$_3$ | |
| 33 | 1 | 1 | O | H | H | (4-)CN | (2-)F | H$_3$C-N, CF$_3$-triazolinone-N-CH$_3$ | |
| 34 | 1 | 1 | O | H | H | (4-)CSNH$_2$ | (2-)F | H$_3$C-N, CF$_3$-triazolinone-N-CH$_3$ | |
| 35 | 1 | 0 | O | H | H | (4-)Cl | — | H$_3$C-N, CF$_3$-triazolinone-N-CH$_3$ | |
| 36 | 1 | 1 | O | CH$_3$ | CH$_3$ | (4-)F | (2-)F | H$_3$C-N, CF$_3$-triazolinone-N-CH$_3$ | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 37 | 2 | 1 | O | H | H | (2-)F, (5-)CN | (2-)F | 4-methyl-2-methyl-5-(trifluoromethyl)-2,4-dihydro-3H-1,2,4-triazol-3-one | |
| 38 | 3 | 1 | O | H | H | (2-,4-)F₂, (5-)CN | (2-)F | 4-methyl-2-methyl-5-(trifluoromethyl)-2,4-dihydro-3H-1,2,4-triazol-3-one | |
| 39 | 1 | 1 | O | H | H | (4-)Cl | (2-)F | 4-methyl-2-methyl-5-(trifluoromethyl)-2,4-dihydro-3H-1,2,4-triazol-3-one | |
| 40 | 1 | 1 | O | H | H | (2-)Cl | (2-)F | 4-methyl-2-methyl-5-(difluoromethyl)-2,4-dihydro-3H-1,2,4-triazol-3-one | |
| 41 | 1 | 1 | O | H | H | (3-)Cl | (2-)F | 4-methyl-2-methyl-5-(difluoromethyl)-2,4-dihydro-3H-1,2,4-triazol-3-one | |
| 42 | 1 | 1 | O | H | H | (4-)CN | (2-)F | 4-methyl-2-methyl-5-(difluoromethyl)-2,4-dihydro-3H-1,2,4-triazol-3-one | |
| 43 | 1 | 1 | O | H | H | (4-)CSNH₂ | (2-)F | 4-methyl-2-methyl-5-(difluoromethyl)-2,4-dihydro-3H-1,2,4-triazol-3-one | |
| 44 | 1 | 0 | O | H | H | (4-)Cl | — | 4-methyl-2-methyl-5-(difluoromethyl)-2,4-dihydro-3H-1,2,4-triazol-3-one | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 45 | 1 | 1 | O | CH₃ | CH₃ | (4-)F | (2-)F | 4-methyl-2-methyl-3-(difluoromethyl)-1,2,4-triazol-5(4H)-one | |
| 46 | 2 | 1 | O | H | H | (2-)F, (5-)CN | (2-)F | 4-methyl-2-methyl-3-(difluoromethyl)-1,2,4-triazol-5(4H)-one | |
| 47 | 3 | 1 | O | H | H | (2-,4-)F₂, (5-)CN | (2-)F | 4-methyl-2-methyl-3-(difluoromethyl)-1,2,4-triazol-5(4H)-one | |
| 48 | 1 | 1 | O | H | H | (4-)Cl | (2-)F | 4-methyl-2-methyl-3-(difluoromethyl)-1,2,4-triazol-5(4H)-one | |
| 49 | 1 | 1 | O | H | H | (2-)Cl | (2-)F | 4-amino-2-methyl-3-(trifluoromethyl)-1,2,4-triazol-5(4H)-one | |
| 50 | 1 | 1 | O | H | H | (3-)Cl | (2-)F | 4-amino-2-methyl-3-(trifluoromethyl)-1,2,4-triazol-5(4H)-one | |
| 51 | 1 | 1 | O | H | H | (4-)CN | (2-)F | 4-amino-2-methyl-3-(trifluoromethyl)-1,2,4-triazol-5(4H)-one | |
| 52 | 1 | 1 | O | H | H | (4-)CSNH₂ | (2-)F | 4-amino-2-methyl-3-(trifluoromethyl)-1,2,4-triazol-5(4H)-one | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 53 | 1 | 0 | O | H | H | (4-)Cl | — | 4-amino-3-(trifluoromethyl)-1-methyl-1,2,4-triazol-5(4H)-one | |
| 54 | 1 | 1 | O | CH₃ | CH₃ | (4-)F | (2-)F | 4-amino-3-(trifluoromethyl)-1-methyl-1,2,4-triazol-5(4H)-one | |
| 55 | 2 | 1 | O | H | H | (2-)F, (5-)CN | (2-)F | 4-amino-3-(trifluoromethyl)-1-methyl-1,2,4-triazol-5(4H)-one | |
| 56 | 3 | 1 | O | H | H | (2-,4-)F₂, (5-)CN | (2-)F | 4-amino-3-(trifluoromethyl)-1-methyl-1,2,4-triazol-5(4H)-one | |
| 57 | 1 | 1 | O | H | H | (4-)Cl | (2-)F | 4-amino-3-(trifluoromethyl)-1-methyl-1,2,4-triazol-5(4H)-one | |
| 58 | 1 | 1 | O | H | H | (2-)Cl | (2-)F | 4-(dimethylamino)-3-(trifluoromethyl)-1-methyl-1,2,4-triazol-5(4H)-one | |
| 59 | 1 | 1 | O | H | H | (3-)Cl | (2-)F | 4-(dimethylamino)-3-(trifluoromethyl)-1-methyl-1,2,4-triazol-5(4H)-one | |
| 60 | 1 | 1 | O | H | H | (4-)CN | (2-)F | 4-(dimethylamino)-3-(trifluoromethyl)-1-methyl-1,2,4-triazol-5(4H)-one | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 61 | 1 | 1 | O | H | H | (4-)CSNH₂ | (2-)F | 4-(dimethylamino)-2-methyl-5-(trifluoromethyl)-2,4-dihydro-3H-1,2,4-triazol-3-one | |
| 62 | 1 | 0 | O | H | H | (4-)Cl | — | 4-(dimethylamino)-2-methyl-5-(trifluoromethyl)-2,4-dihydro-3H-1,2,4-triazol-3-one | |
| 63 | 1 | 1 | O | CH₃ | CH₃ | (4-)F | (2-)F | 4-(dimethylamino)-2-methyl-5-(trifluoromethyl)-2,4-dihydro-3H-1,2,4-triazol-3-one | |
| 64 | 2 | 1 | O | H | H | (2-)F, (5-)CN | (2-)F | 4-(dimethylamino)-2-methyl-5-(trifluoromethyl)-2,4-dihydro-3H-1,2,4-triazol-3-one | |
| 65 | 3 | 1 | O | H | H | (2-,4-)F₂, (5-)CN | (2-)F | 4-(dimethylamino)-2-methyl-5-(trifluoromethyl)-2,4-dihydro-3H-1,2,4-triazol-3-one | |
| 66 | 1 | 1 | S | H | H | (4-)Cl | (2-)F | 4-(dimethylamino)-2-methyl-5-(trifluoromethyl)-2,4-dihydro-3H-1,2,4-triazol-3-one | |
| 67 | 1 | 1 | O | H | H | (2-)Cl | (2-)F | 4-amino-5-(difluoromethyl)-2-methyl-2,4-dihydro-3H-1,2,4-triazol-3-one | |
| 68 | 1 | 1 | O | H | H | (3-)Cl | (2-)F | 4-amino-5-(difluoromethyl)-2-methyl-2,4-dihydro-3H-1,2,4-triazol-3-one | |

TABLE 1-continued

Examples of the compounds of the formula (I)

| Ex. No. | m | n | Q | $R^1$ | $R^2$ | (position) X | (position) Y | Z | Physical data |
|---|---|---|---|---|---|---|---|---|---|
| 69 | 1 | 1 | O | H | H | (4-)CN | (2-)F | | |
| 70 | 1 | 1 | O | H | H | (4-)CSNH$_2$ | (2-)F | | |
| 71 | 1 | 0 | O | H | H | (4-)Cl | — | | |
| 72 | 1 | 1 | O | CH$_3$ | CH$_3$ | (4-)F | (2-)F | | |
| 73 | 2 | 1 | O | H | H | (2-)F, (5-)CN | (2-)F | | |
| 74 | 3 | 1 | O | H | H | (2-,4-)F$_2$, (5-)CN | (2-)F | | |
| 75 | 1 | 1 | S | H | H | (4-)Cl | (2-)F | | |

TABLE 1-continued

Examples of the compounds of the formula (I)

| Ex. No. | m | n | Q | R¹ | R² | (position) X | (position) Y | Z | Physical data |
|---|---|---|---|---|---|---|---|---|---|
| 76 | 0 | 1 | 0 | H | H | — | (2-)F | [structure: triazolidinedione with CH₃, F₂CH, N-methyl substituents] | M.p.: 124° C. |

Starting Materials of the Formula (II)

Example (II-1)

[structure of 1-ethoxycarbonyl-2-methyl-4-[4-(4-chlorophenyl-methoxy)-2-fluoro-phenyl]-semicarbazide]

4.0 g (16 mMol) of 1-amino-2-fluoro-4-(4-chloro-phenyl-methoxy)-benzene are initially charged in 100 ml of ethyl acetate and, at room temperature (about 20° C.), admixed dropwise with stirring with 6.3 g (32 mMol) of trichloromethyl chloroformate. The mixture is heated under reflux for 2 hours, cooled and concentrated under water pump vacuum. 100 ml of toluene and 2.2 g (16 mMol) of ethyl 2-methylhydrazinecarboxylate are added to the residue, and the reaction mixture is then heated under reflux for 3 hours and stirred during this time. After cooling, the mixture is concentrated under water pump vacuum, and the residue is taken up in ethyl acetate and filtered through silica gel. The solvent is carefully distilled off from the filtrate under water pump vacuum.

This gives 6.0 g (95% of theory) of 1-ethoxycarbonyl-2-methyl-4-[4-(4-chlorophenyl-methoxy)-2-fluoro-phenyl]-semicarbazide as a crystalline residue of melting point 108° C.

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage by comparison with the development of the untreated control.

The figures denote:

0%=no effect (like untreated control)

100%=total destruction

In this test, at application rates between 1000 g and 2000 g per hectare, the compounds of Preparation Example 2 and 3, for example, exhibit strong activity against weeds such as Abutilon (100%), Amaranthus (100%), Sinapis (100%) and Galium (100%), and they are tolerated well by crop plants.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, at application rates of 500 g/ha, the compounds of Preparation Example 2 and 3, for example, exhibit strong activity against weeds such as Abutilon (100%), Amaranthus (100%), Datura (100%), Solanum (100%), Xanthium (100%) and Setaria (95%), and they are tolerated well by crop plants.

What is claimed is:

1. An arylalkyl compound of the formula (I)

(I)

wherein m represents the numbers 0 to 5, n represents the numbers 0 to 4,

Q represents O, S, SO or SO$_2$,

R$^1$ represents hydrogen or represents unsubstituted or halogen-substituted alkyl having 1 to 6 carbon atoms, R$^2$ represents hydrogen or represents unsubstituted or halogen-substituted alkyl having 1 to 6 carbon atoms, X represents hydroxyl, mercapto, amino, hydroxyamino, nitro, formyl, carboxyl, cyano, carbamoyl, thiocarbamoyl, halogen, or represents unsubstituted or cyano-, halogen- or C$_1$–C$_4$-alkoxy-substituted alkyl, alkoxy, alkylthio, alkylsulphinyl, alkylsulphonyl, alkylamino, dialkylamino, alkylcarbonyl or alkoxycarbonyl having in each case 1 to 6 carbon atoms in the alkyl groups, Y represents nitro, carboxyl, cyano, carbamoyl, thiocarbamoyl, halogen, or represents unsubstituted or cyano-, halogen- or C$_1$–C$_4$-alkoxy-substituted alkyl, alkoxy, alkylthio, alkylsulphinyl or alkylsulphonyl having in each case 1 to 6 carbon atoms in the alkyl groups, and Z represents one of the groupings below wherein R$^3$ represents hydrogen, cyano, formyl, or represents unsubstituted or cyano-, halogen- or C$_1$–C$_4$-alkoxy substituted alkyl, alkylcarbonyl or alkoxycarbonyl having in each case 1 to 6 carbon atoms in the alkyl groups, or represents in each case unsubstituted or halogen-substituted alkenyl or alkynyl having in each case 2 to 6 carbon atoms, R$^4$ represents hydrogen, cyano, formyl, or represents unsubstituted or cyano-, halogen- or C$_1$–C$_4$-alkoxy-substituted alkyl, alkylcarbonyl or alkoxycarbonyl having in each case 1 to 6 carbon atoms in the alkyl groups, or represents in each case unsubstituted or halogen-substituted alkenyl or alkynyl having in each case 2 to 6 carbon atoms.

2. An arylalkyl compound comprising the formula

3. A process for preparing an arylalkyl compound of the formula (I)

(I)

wherein m, n, Q, R$^1$, R$^2$, X, Y and Z are each as defined in claim 1, comprising the step of cyclocondensing a 4-aryl-semicarbazide of the formula (II)

(II)

wherein m, n, Q, R$^1$, R$^2$, R$^3$, R$^4$, X and Y are as defined in claim 1, and R represents alkyl.

4. The arylalkyl compound of claim 1 wherein m represents the numbers 0 to 4 and n represents the numbers 0 to 3.

5. A herbicidal composition comprising an arylalkyl compound of claim 1 and a member selected from the group consisting of a liquid solvent, a solid carriers, a surfactant and mixtures thereof.

6. A method for controlling undesirable plants, comprising the step of allowing an effective amount of an arylalkyl compound of claim 1 to act on undesirable plants and/or their habitat.

7. The process of claim 3 wherein the reaction is carried out in the presence of a member selected from the group consisting of an inert organic solvent, an inorganic base, an organic base and mixtures thereof.

\* \* \* \* \*